United States Patent [19]
Fredriksen et al.

[11] Patent Number: 6,021,380
[45] Date of Patent: Feb. 1, 2000

[54] AUTOMATIC SEMICONDUCTOR WAFER SORTER/PROBER WITH EXTENDED OPTICAL INSPECTION

[75] Inventors: T. Roland Fredriksen, Saratoga; Robert L. Chapman, San Mateo, both of Calif.

[73] Assignee: Scanis, Inc., Foster City, Calif.

[21] Appl. No.: 08/886,066

[22] Filed: Jul. 2, 1997

Related U.S. Application Data

[60] Provisional application No. 60/022,701, Jul. 9, 1996.

[51] Int. Cl.⁷ .................................................. G01R 31/26
[52] U.S. Cl. .......................... 702/35; 356/237.7; 356/390
[58] Field of Search .......................... 702/35; 356/237.2, 356/390; 600/407

[56] References Cited

U.S. PATENT DOCUMENTS

| | | |
|---|---|---|
| 4,677,474 | 6/1987 | Sato et al. . |
| 4,805,123 | 2/1989 | Specht et al. . |
| 4,929,893 | 5/1990 | Sato et al. . |
| 5,012,523 | 4/1991 | Kobayashi et al. . |
| 5,212,637 | 5/1993 | Saxena ..................................... 600/407 |
| 5,219,765 | 6/1993 | Yoshida et al. . |
| 5,240,866 | 8/1993 | Friedman et al. . |
| 5,390,131 | 2/1995 | Rohrbaugh et al. . |
| 5,511,934 | 4/1996 | Bacchi et al. . |
| 5,754,298 | 5/1998 | Falk .......................................... 356/390 |
| 5,808,735 | 9/1998 | Lee et al. .............................. 356/237.2 |

*Primary Examiner*—Thomas R. Peeso
*Attorney, Agent, or Firm*—Flehr Hohbach Test Albritton & Herbert LLP

[57] ABSTRACT

A method and apparatus for visually inspecting and sorting semiconductor wafers and the individual microcircuits or chips thereon. The preferred embodiment employs a scanner to obtain a virtual reality image of the wafer and all chips are identified and sorted by applying high-speed image processing routines. The resulting wafer map provides unique image controlled chip coordinates making the chips identifiable even after the chips are diced apart. The wafer may contain different kinds of chips in irregular patterns. A gross-defect, visual inspection sorts out defective chips based on image completeness maximizing the yield and throughput. All inspections and identifications are performed on the virtual wafer or chip images scanned into a computer memory with full physical wafer correlation but without having to manipulate the wafer. The inspection time is, therefore, largely free due to overlapping it by regular transport operations.

7 Claims, 9 Drawing Sheets

AUTOMATIC SEMICONDUCTOR WAFER SORTER/PROBER WITH EXTENDED OPTICAL INSPECTION

RELATED APPLICATION

Priority is claimed to Provisional Application Serial No. 60/022,701 filed Jul. 9, 1996 for Automatic Semiconductor Wafer Prober with Extended Optical Inspection.

BACKGROUND OF THE INVENTION

In the fabrication of semiconductor circuits and other chips such as memory chips, many chips are formed in a checker-board fashion on a generally round wafer of semiconductor material. During the assembly process these chips are cut apart and placed on lead-frames or the like, then packaged and tested. To save the cost of packaging defective chips the wafer is tested by a wafer prober before being diced. In the wafer prober, the bonding pads of each chip are brought into contact with a set of test needles which, in turn, are connected to an electronic tester. The functionality of the chip is checked and failed chips are marked with an ink dot. Often, instead of immediately inking the failed chips, a positional map of the wafer is stored in the system memory and is reused and updated in secondary tests or assembly operations.

Most wafer probers include a loader portion and a prober portion. In addition, they are fully automatic and process the wafers in lots of 25 or 50. The wafers are transported in cassettes and placed in a loader portion of the of the prober. A robotic wafer handler transports each wafer sequentially from storage cassettes to a pre-aligner, where the wafer is centered and pre-oriented by locating the flat or other physical marks such as a notch. The wafer is then delivered to a prober stage approximately centered and with the chip checker pattern approximately parallel to the X-Y stage motion. The orientation is coordinated to suit the test needles and chip test pads.

From the time a new wafer is delivered to the prober stage and until it is returned fully tested, the prober and loader portions operate independently. The prober stage first brings the wafer under an alignment unit where the actual chip pattern is detected and accurately aligned to suit the test needle array. Then, each chip is sequentially brought into contact with the probes of the needle array and are functionally checked by the tester. Depending on the testing complexity and wafer size this may take a few minutes to more than hour. The loader operation on the other hand takes less than a minute regardless of chip complexity. A wafer therefore sits idle in the loader for many hours.

The conventional loader provides no detailed information about the chips to the probing control which must calculate the chip position relative to the wafer edge without knowledge of the chip pattern near the edge. Many of the chips along the wafer edge are incomplete and test defective even though the calculation has determined them as physically complete and potentially good. It is a waste of time to test an incomplete chip and an incomplete chip may even cause damage to the sensitive probe needles slipping over the edge. To avoid this, the prober does not put partial edge chips in contact with the needles. However, the inaccurate knowledge of the chip's physical condition may lead to some good chips not being tested and arbitrarily marked defective. To improve this situation a control map is manually generated to steer the prober to the testable chips. Such a control map, however, does not adequately take care of wafer to wafer differences and is itself time consuming to generate.

A chip may have been subjected to damage both before and during probing. When such a chip fails the electrical wafer test it causes inefficiency. But such damage might not affect the chip operation until after the chip has been packaged and installed, consequently, it is not sensed by the electrical wafer test. To prevent such defects which escape detection in the electrical test, the wafers are subjected to visual inspection both pre- and post-probing. In the pre-probe case this is usually done without exact knowledge of chip to chip relation and thus has virtually no value in wafer chip sorting. The post-probe inspection is largely manual as no reliable automatic methods have been found that compares with the electrical probing test. The post-probe inspection is therefore a separate processing step requiring extra wafer lot handling and equipment.

This invention relates to finding visual defects in semiconductor wafers and chips and to sorting out those defective wafers or chips which would cause failure in later applications. One inspection object is semiconductor wafers and the task is to sort out defective chips before they are diced apart. Another inspection object is printed circuit boards (PCB) where it is necessary to visually detect flaws in artwork as well as the finished product. Common to both fields is the goal of maximizing the output of long term "good products" and eliminate the passage of potentially "defective products" which can cause serious economic consequences in later assemblies.

BRIEF SUMMARY OF THE INVENTION

The automatic wafer sorter in accordance with the invention performs optical inspection for visual defects on the chips during their idle time in the loader portion of an automatic prober. An image analysis program emulates a skilled human inspector's methodology in discovering and classifying defects. A 95% certainty of catching a damaging defect in a chip is expected. It is a fully automatic operation, which can safely be integrated in the prober.

In accordance with the invention, a pre-probe optical inspection generates a unique chip location map for each wafer which completely resolves the uncertainty about testable chips. The scanned images provide an absolutely dependable chip coordinate reference system, which makes the wafer map usable even after the wafer has been diced. The inspection system can therefore be used to inspect dicing damage after the chips have been cut apart and the wafer map can be applied to pick-and-place assembly machines.

The loader portion of the sorter can be used as a free standing optical inspection station suitable for clean room operation as well as wafer sorting in general. Thus, chip allocated defects can be recorded in a wafer map after the first metalization with wafer ID. Furthermore, since the inspections are performed on the virtual wafer image in memory, the physical wafer need not be oriented nor aligned, making it practical to implement this feature in existing wafer processing equipment.

The post-probe inspection unit can also be mounted in an automatic-prober head plate taking the place of probe needle and tester. This provides the means for utilizing automatic probers which is not sufficiently accurate for advanced chip designs.

The same combination of high resolution scanner and high magnification camera is projected to increased reliability and give a more economical operation when inspecting films and PCB's in the circuit board manufacturing.

It is one object of the invention to define an automatic optical inspection system capable of detecting and classifying visual defects on semiconductor wafers, printed circuit boards (PCB) and similar product elements. The inspection process is an adaptation of a system described in U.S. Pat. No. 5,212,637 issued May 18, 1993 and known generally as the MAMMEX™ system.

Another object of the invention is to provide a gross defect inspection unit which makes a complete scan of each wafer and stores the digital images in a computer memory. All inspections and analyses are performed on these virtual wafer images resolving orientation, chip location, defects and wafer identification (ID). As a pre-probe optical inspection unit the wafer is aligned according to die pattern rather than just the "flat" angle. This removes the problems and delays caused by the variable flat angle with the pattern. The visual inspection of each chip forms the basis for very accurate determination of all testable chips which allows the prober to maximize yield and throughput. As a general wafer sorter the gross defect inspection station checks wafer ID and produces unique wafer control maps.

Still another object of the invention is to implement an image supported chip coordinate reference system which avoids ambiguities and guaranties correct chip identification in later processing steps. The reference system is effective even after the chips have been diced apart and can be employed by pick-and-place assembly machines.

In addition, apparatus in accordance with the invention generates an image based wafer mapping system capable of directly reading wafer ID in either optical character recognition (OCR) or bar code recognition (BCR) thereby eliminating the need for separate OCR and BCR stations. Likewise, gross defects are classified and marked in the wafer map.

Yet another object of the invention is to provide a chip inspection station for locating visual defects in single chips using the virtual image obtained by a charge control device (CCD) camera—optical system. Used as a Post-Probe chip inspection system, the inspection time is "free" by utilizing the otherwise idle wafer time. An optional inker can be programmed to mark both electrically and visually defective chips. This operation further increases the throughput of the wafer probing phase of the sorting process.

Furthermore, the invention provides a free standing visual inspection system requiring minimal wafer handling and positioning suitable throughout the wafer processing cycle.

BRIEF DESCRIPTION OF THE DRAWING

Additional objects and features of the invention will be more readily apparent from the following detailed description and the claims when taken in conjunction with the drawing in which:

DESCRIPTION OF THE PREFERRED EMBODIMENTS

Figure 1:
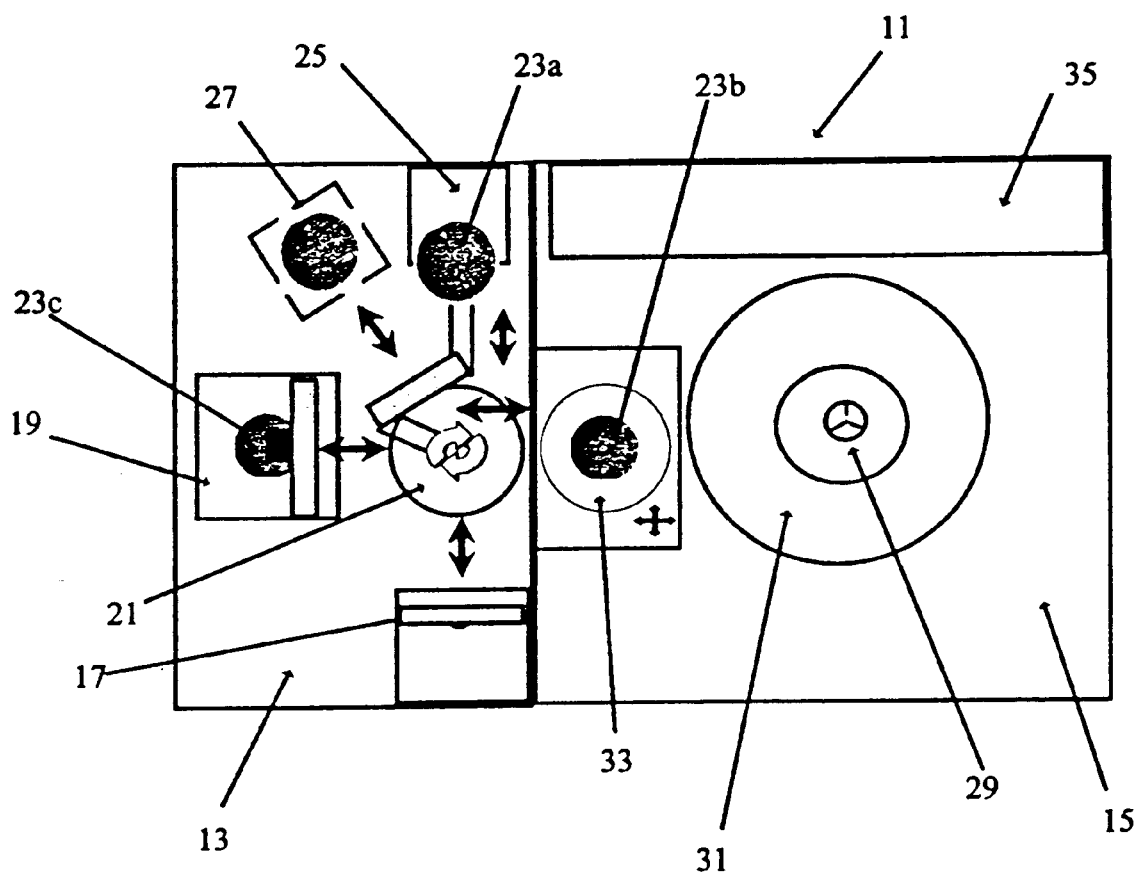
FIG. 1 is a schematic top plan view of an automatic wafer prober/sorter in accordance with the invention.

Referring to FIG. 1, there is shown the overall arrangement of a wafer sorter/prober 11 including a loader portion 13 and a prober portion 15. The loader portion 13 includes a "pre-probe", gross defect—inspection unit 17 and a "post-probe", single chip—inspection unit 19. The inspection units 17 and 19 can be allowed to operate within the automatic prober because they require no more manual intervention than the typical automatic prober. The inspection process is carried out entirely within the idle time of the wafers and actually increases the throughput and yield of the electrical test operation by eliminating waste and maximizing the potential "good" chips.

The loader portion 13 has a robotic wafer handler 21 which serves to transport a wafer 23a from one of two storage cassettes 25 or 27 first to the pre-probe inspection unit 17 and later to the prober portion 15. Still later, the handler 21 serves to move the wafer from the prober portion 15 to the post-probe inspection unit 19.

The prober portion 15 includes the usual probe card 29 held securely by a probe card ring 31. In addition, it includes a prober stage 33 and an alignment unit 35 which perform the usual functions of properly aligning the wafer 23b and positioning it for electrical testing by placing each bonding pad of the wafer into contact with the probe needles on the probe card 29.

The pre-probe, gross defect inspection unit 17 performs the pre-alignment, identification, mapping and gross defect inspection of each wafer. Each task yields improvements to the conventional wafer sorting or probing operations.

With pre-alignment, the wafer can be aligned to the chip pattern flat in addition to the orientation flat, thereby avoiding rejects and speeding up wafer alignment in the prober. (The flat is not always very accurately parallel to chip pattern)

The wafer identification location can be accessed directly from the scanned image. No separate OCR or BCR readers are required. The inspection software makes the image acquisition and identification from the virtual wafer image while or after the wafer is moved on to other operations.

A unique wafer map is generated from each wafer, which precisely identifies chip centers with actual wafer outline. A potential good chip is judged from completeness of actual pattern image and the coordinate reference based on actual re-recognizable edge images.

The pre-probe unit utilizes a rigorous image based coordinate system. Images show standard chips where sub-images are given arbitrary numerical values (e.g. 1, 2, 4, 8 and 16) to identify the completeness of the chip. If a sub-image is missing or flawed, the chip's "score" is reduced by that value. The image illustrates the values of some edge chips. Clearly, the reference system provides unique identification even after the wafer is diced apart.

Gross defect damages such as multi-chip scratches, large foreign materials and metalization errors are located through search procedures simulating the visual inspection by an operator looking for such defects. Random defects are noted in the wafer map for potential test exclusion if it cannot be positively identified as a pattern defect. Repeatable damages can be correlated and flagged to QC (quality control).

Figures 2A, 2B:
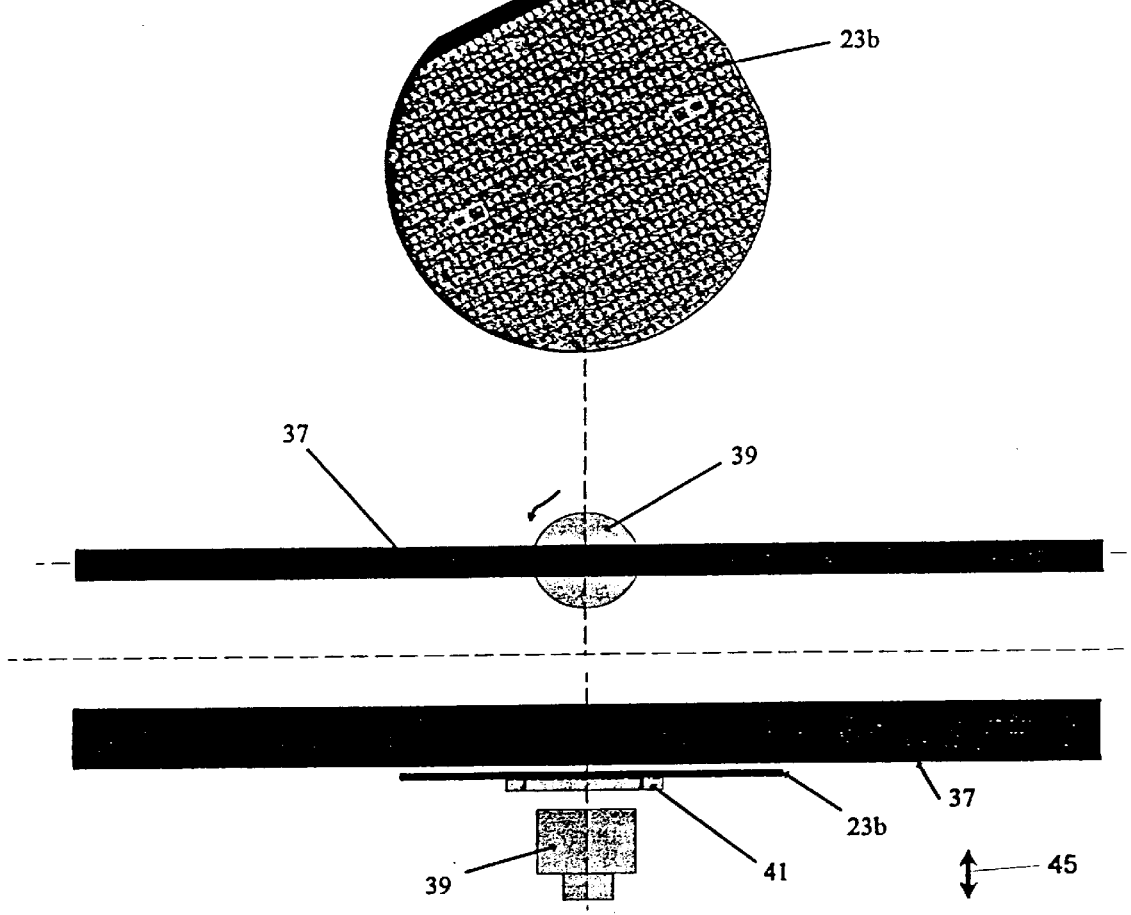
FIG. 2A is a schematic top plan view of a pre-probe inspection unit for detecting gross defects in accordance with the invention.
FIG. 2B is a schematic side view of the pre-probe inspection unit of FIG. 2A.

FIGS. 2A and 2B show one embodiment of the pre-probe, gross defect, inspection element 17 of FIG. 1. The wafer 23b is held with vacuum by a handler arm 41, which has the ability to move the wafer under the scanner rail 37 at a constant speed and at the correct vertical (Z) displacement for reading the image data. The arm clears the vacuum chuck 39 by a comfortable margin.

Referring specifically to FIGS. 2A and 2B, the pre-probe inspection unit 17 includes a scanner array 37 and a vacuum chuck 39 which can be commanded to rotate a precise number of degrees. The robotic wafer handling arm 41 provides horizontal Y-motion of the wafer, as shown by the arrow 43, as well as the required vertical Z-displacement, as shown by the arrow 45. The robotic wafer handling arm 41 which holds the wafer 23b by vacuum moves the wafer to the pre-probe station 17, then, at constant speed, moves the wafer past the scanner array while the scanner records the reflected wafer image in memory.

As an alternative, the scanner rail 37 can make the motion which may in some installations be more practical, considering available space and existing elements in the prober.

Figure 3:
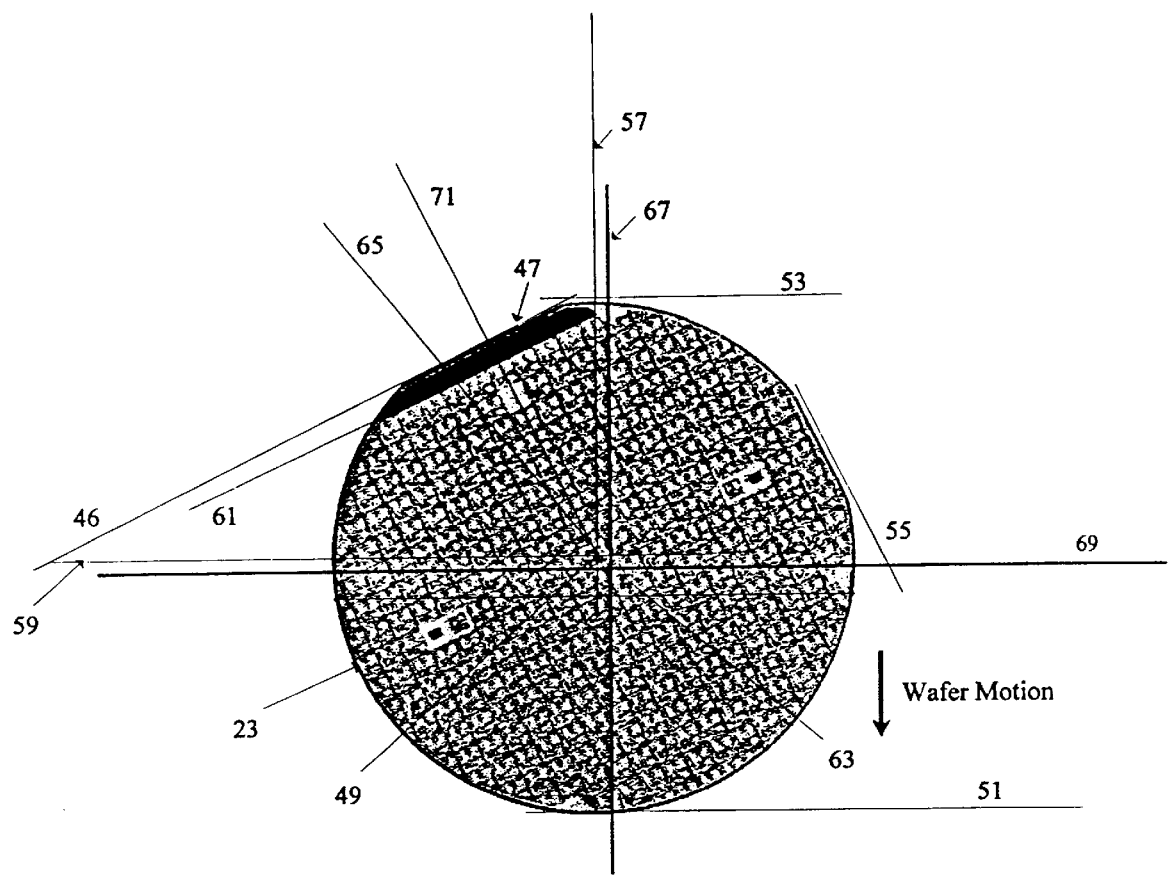
FIG. 3 is a view of a wafer image as used for identifying the wafer and analyzing the image data thereon.

Referring to FIG. 3, there is shown an example of an image from the pre-probe scanner 17 prior to any orientation correction. The resulting scan is first used to calculate the position of the flat and the wafer center as well as the relative positions of the wafer and chuck centers. In this case the image data is not used with full resolution and a pixel thresh-hold is used rather than the full details of the gray scale value. The image control software calculates the angle of the flat and rotates the image data to a normalized position, then the precise chip locations are determined. In the prober, the wafer must be delivered at a certain orientation to match the needles to the pads. Hence, the system controller receives the angular and center corrections needed to operate the chuck 39 and handler arm 41 so that wafer 23b can be delivered to the prober stage 33 centered and be properly oriented to the probe card 29. This operation is not necessary if the wafer is returned to one of the storage cassettes 25 or 27 rather than being immediately electrically tested.

A separate microprocessor controls the pre-probe inspection station 17 interfacing with the handler 21, scanner 37, vacuum chuck 39 and a dedicated image-processing unit. The control system executes only one scanning operation, storing the data sequentially in a two dimensional array so that the array addressing relates uniquely to the handler arm position in one dimension and the individual pixel data points in the scan line in the other. To this effect, the hardware is so arranged that the center pixel of the scanning array 37 is stored at the half point in the allocated memory block (array) as illustrated in FIG. 3. The center of the vacuum chuck 39 lies on the scanner array pixel-line.

The image analysis is to determine the position of the orientation flat 47 and the center of the wafer 49. This is accomplished by examining each scan line of data from the first reflection found at starting line position 51 to the last line at position 53. Between scan lines 51 and 53 the image reveals two flats, a minor one 55 and the major orientation flat 47. From line 51 to the flat 55 the half point calculation gives a constant value for the X-center line of the wafer each half changing in value according to the symmetry of a circle. Beginning at the flat 55, the right half changes faster than a circle and, from the beginning of flat 47, the left half deviates from the circle. From this data the larger flat 47 is recognized as the desired orientation flat and the end point coordinates yield the exact flat angle. Likewise, the symmetry of data locations converts into the wafer center position 49 by having determined the X-center line 57 and the Y-center line 59 of the wafer 23.

It should be pointed out that for the wafer shown in FIG. 3 the black, largely non-reflective stripe inside the flat 47 is easily detected as a wafer ID field and thus line 61 is determined as the "pattern flat" which is more desirable and more accurate. This is an additional benefit from scanning a wafer instead of the customary detection of edge.

Figure 4:
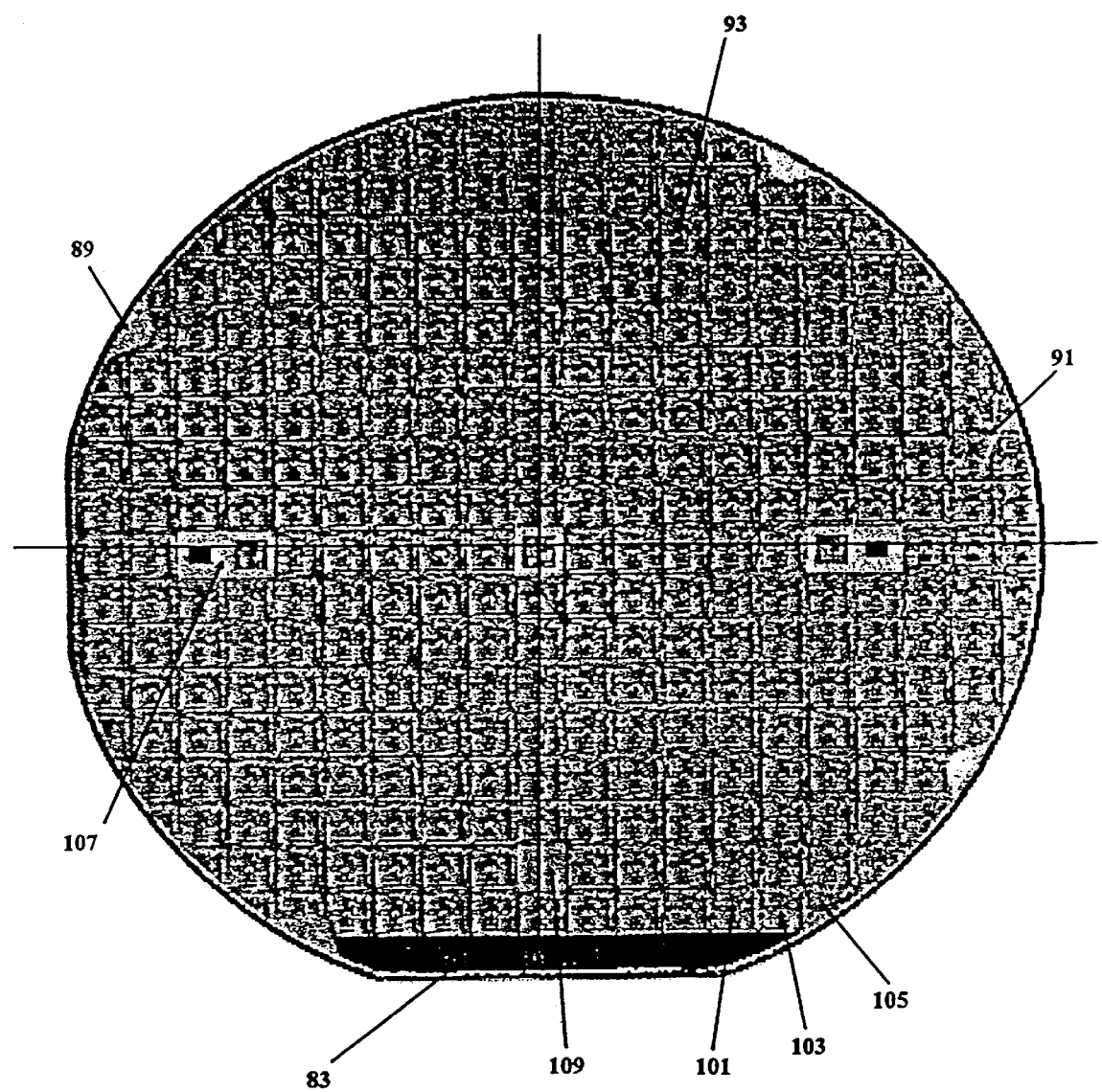
FIGS. 4A and 4B are top plan views of a wafer image similar to FIG. 3 but showing details of information which can be obtained from the image.
Figure 4:
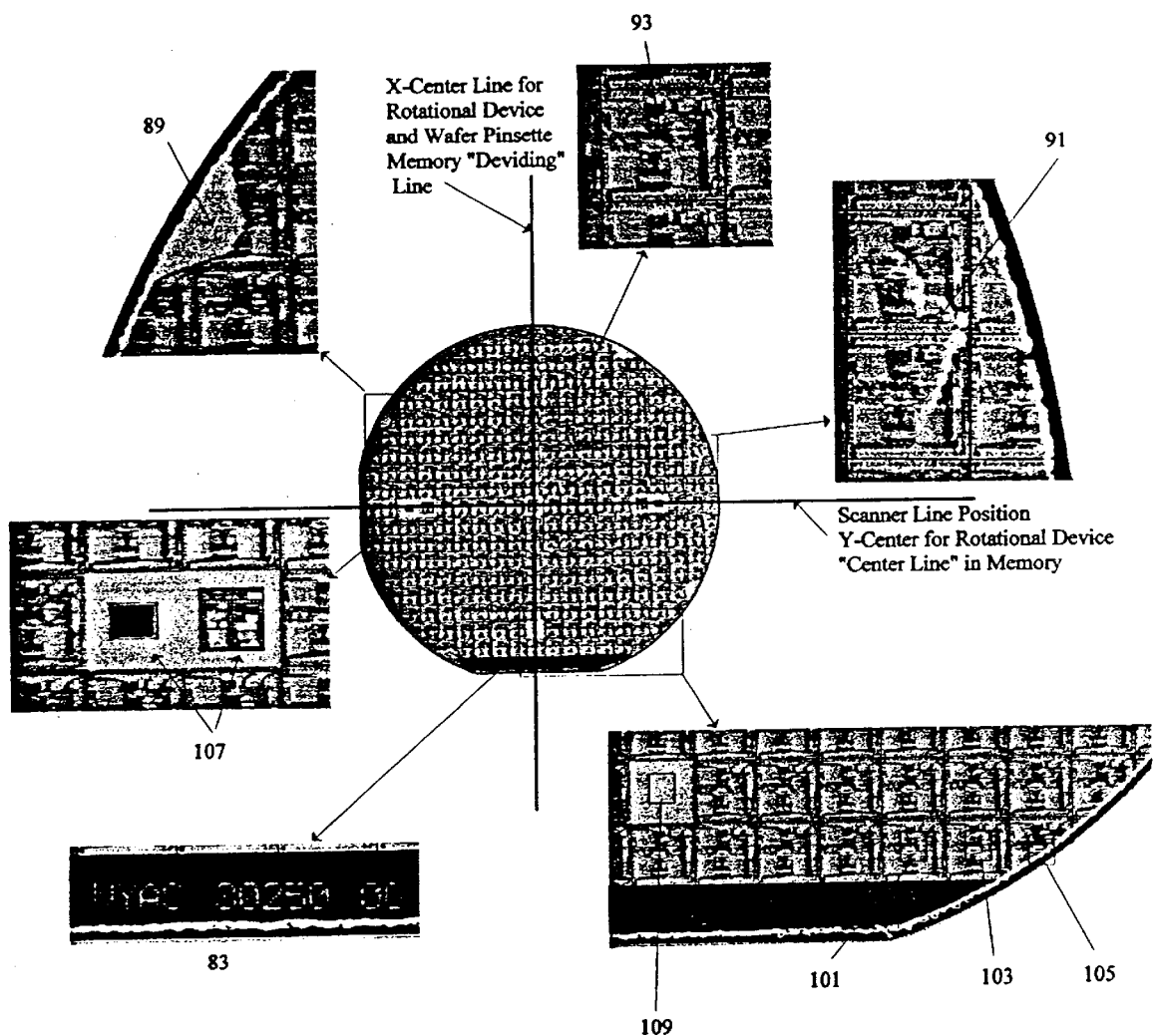

Having found the data location representing the wafer image center 49 and the flat angle, the image is rotated around the center 49 until the virtual wafer has an image shown in FIG. 4. This makes the chip search sometimes easier. When the real wafer must be reoriented, as is the case for the prober application, the image control must supply two angles and one Y-motion offset. Since the wafer can only be moved along the Y-axis it is first necessary to rotate the wafer clockwise (the shorter angle to the Y-axis in this example) around the chuck center 63 until line 65 passing through the chuck center 63 and the wafer center 49, coincides with the X-center line 67 of the chuck 39. This is executed by lowering the wafer vertically transferring the vacuum hold from the handler arm to the chuck. The chuck is then controlled to rotate the exact clockwise degrees around its center 63 formed by the Y-axis 67 and the X-axis 69 of the chuck 39. Next, the handler arm 41 again picks up the wafer and displaces it along the Y-axis 67 until the wafer center 49 coincides with the chuck center 63. Finally, the handler arm 41 transfers the wafer to the chuck 39 which can be controlled to rotate the orientation flat 47 or the pattern flat 61 to its final position prescribed by the probing operation. To arrive at the position in FIG. 4 this amounts to counterclockwise rotation of 180° plus the angle between the line 71 passing through wafer center 49 and perpendicular to the pattern flat 61 and the line 65.

As seen in FIG. 4, the image data from the rotated virtual wafer in memory provides sufficient information to determine the exact chip positions, wafer I.D. and gross defects.

Simultaneously with the operation of the pre-probe inspection unit 17, the post-probe inspection unit 19 will proceed independently to inspect a wafer. Key to the embodiment in FIG. 1 is the asynchronous operation of electrical testing by the prober section 15 and the inspections in the loader portion 13. The prober is the pacing operation and the priorities of the handler are to unload and load wafers, maximizing the wafer throughput. The second wafer storage cassette 27 provides the means for continuous operation between lots.

After the wafer has been electrically tested it is directly delivered to the post-probe inspection station 19 (FIG. 1). The wafer is there held by vacuum while the robotic wafer handler 21 delivers the next wafer to the probing operation and pre-orients and inspects the following wafer in the pre-probe inspect station 17. The essential post-probe inspection station configuration is outlined in FIG. 5.

Figure 5:
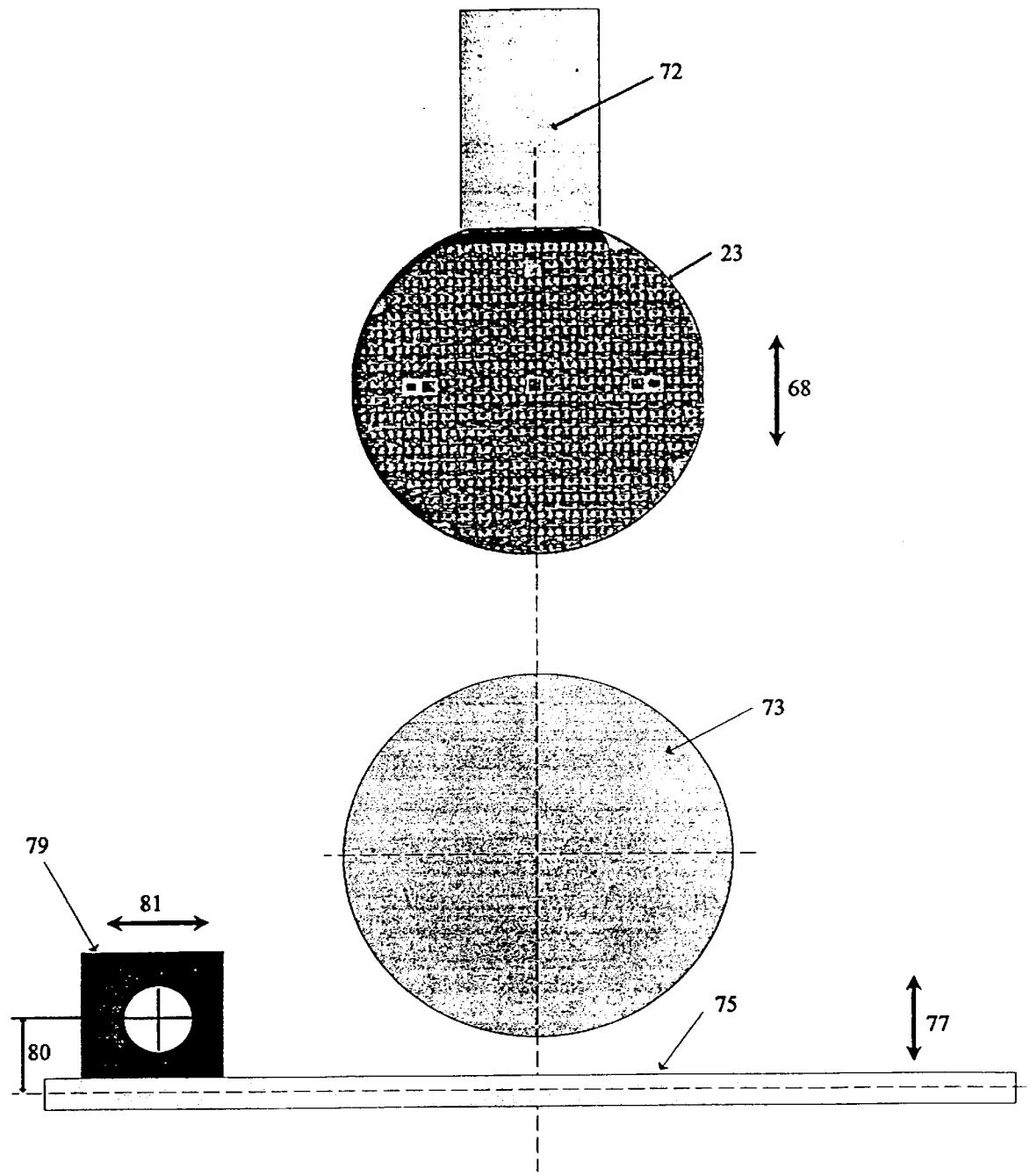
FIG. 5 is a schematic top plan view of a post-probe inspection unit for inspecting single chips in accordance with the invention.
Figure 6:
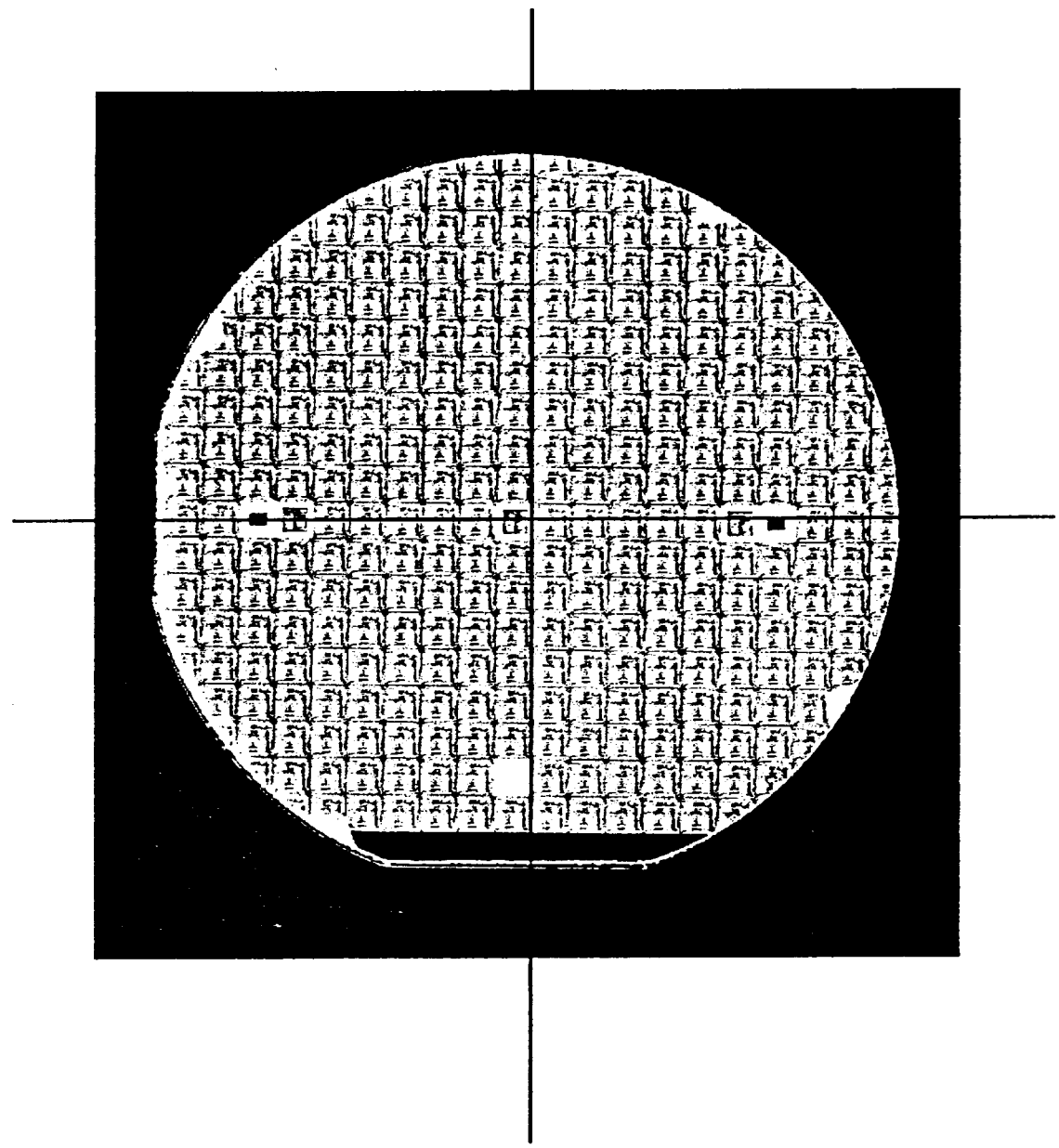
FIG. 6 is a view of a wafer image from the post-probe inspection unit.

One embodiment of the post-probe inspection station is shown in FIG. 5. As detailed, the wafer handler 72 is ready to deliver a wafer 23 to the large vacuum chuck 73. The wafer may be pre-aligned by virtue of just having been electrically tested or be randomly oriented. The wafer handler 72 transfers the wafer 23 to the vacuum chuck 73 and a dedicated control system proceeds with the post-probe defect inspection. It should be noted that even though the vacuum chuck 73 is somewhat larger in diameter than the wafer for stability purposes when supporting finer focus requirements for high magnification, the outer rim is black and does not reflect; hence, scanning the wafer gives an image of the wafer as shown in FIG. 6.

Figure 7A:
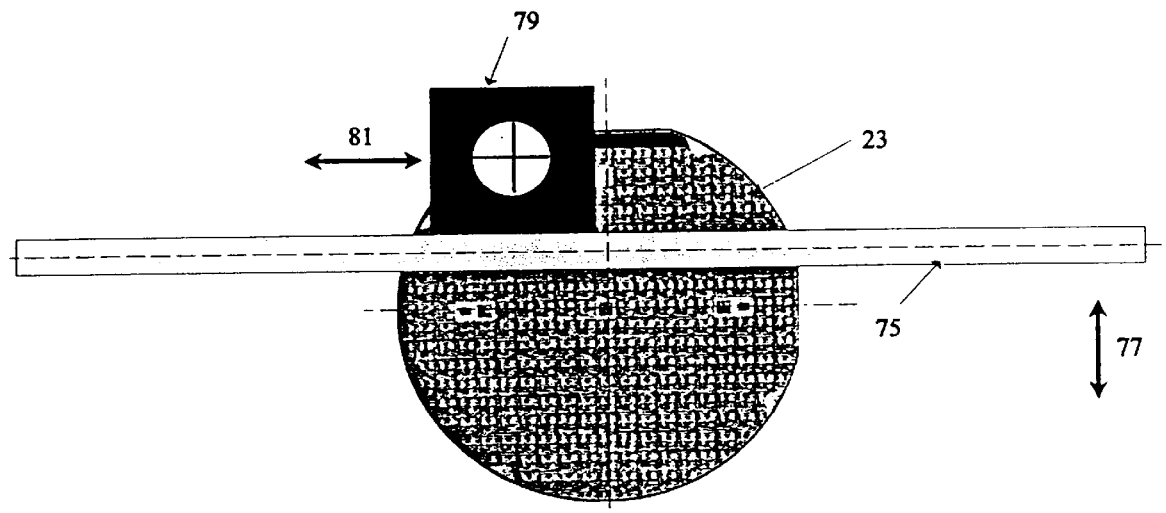
FIG. 7A is a top view of a post-probe inspection unit showing a camera positioned to view a single chip.
Figure 7B:
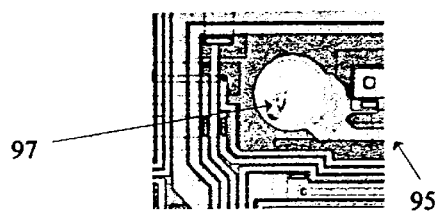
FIG. 7B is a view showing the detail of the single chip being viewed as shown in FIG. 7A.

The inspection sequence begins by making a complete scan like the gross defect inspection station. As in the pre-probe station, the memory addressing relates uniquely to X-Y positioning mechanisms, but in this case, the scanner rail 75 moves in the Y-direction 77 while the chuck is stationary. The X-dimension is given directly by the pixel elements in the scanner array. The virtual wafer image shown in FIG. 6 is correlated with the test map resulting from the probing identifying the X-Y center coordinates of the chips to be inspected. From this information a table is generated which is sequentially used to position the CCD camera 79 so that its center coincides with the center pixel of the chip. The rail motion as shown by the arrow 77 is recalculated to include the fixed camera offset 80 and the angular position of the physical wafer. During a one-time setup procedure the camera optics, which includes a zoom lens, is adjusted to capture one chip and the offset is adjusted aligning the camera picture center with the chip center. The accuracy requirement is determined by uniquely capturing the image of one targeted chip and seeing all of the chip. It is to be understood that micro motion can also be installed in the camera. FIG. 7A shows the camera 79 being positioned by the scanner rail 75 over the wafer 23. Referring to FIG. 7B, a detail of the current image 95 as seen by the camera shows a questionable probe mark 97.

The single chip inspection station is completely self-sufficient and can generate its own wafer map or correlate the wafer with a previously generated wafer map. Thus, a previously inked wafer can be processed directly, inspecting both ink dots from the scanner image representing failed chips, and chip details from good chips using the camera image.

Figure 8A:
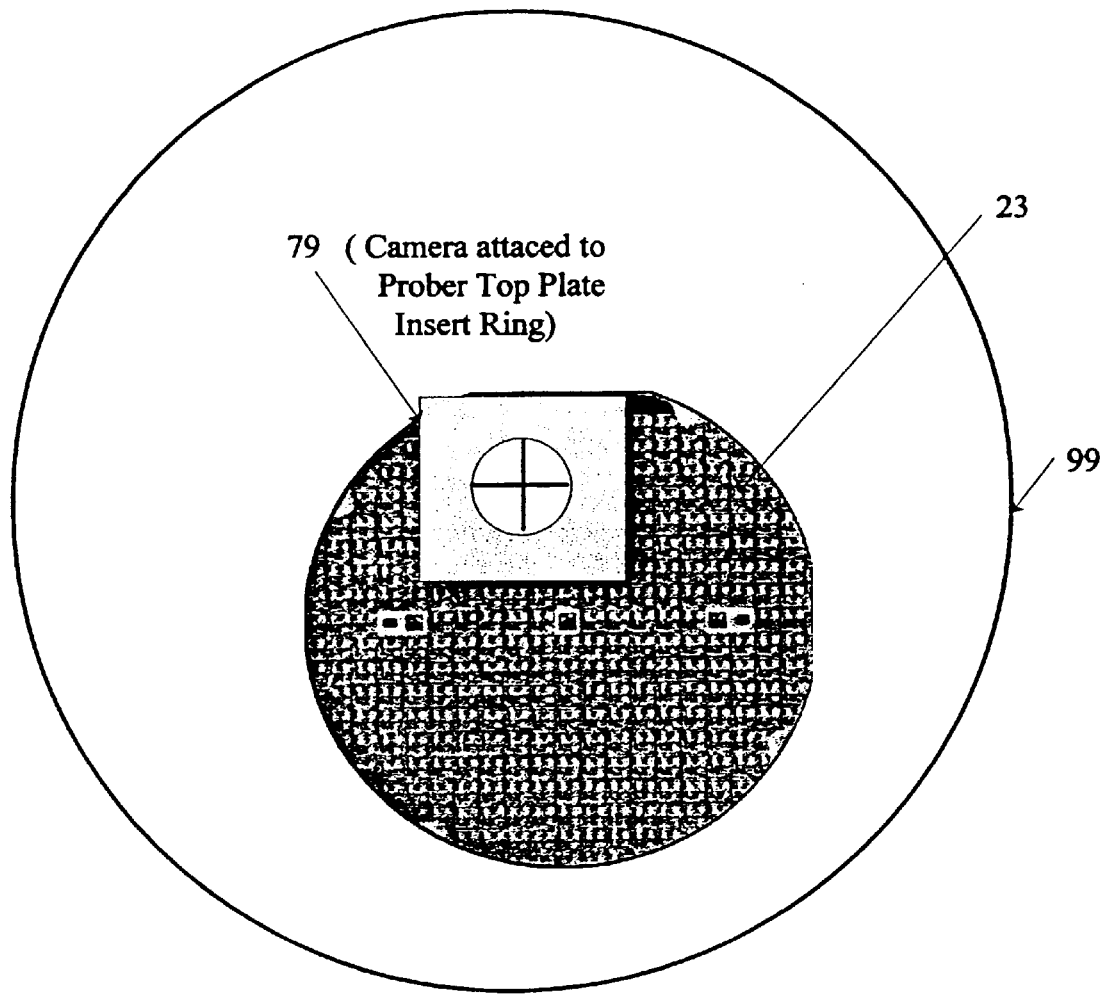
FIG. 8A is a view similar to FIG. 7A but showing an alternative mounting for the camera.
Figure 8B:
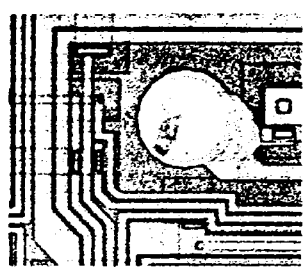
FIG. 8B is a view showing the detail of the single chip being viewed as shown in FIG. 8A.

Another embodiment of the post-probe or single chip inspection system is detailed in FIG. 8A. In this case, the camera 79 is fixed in the probing center by a special insert ring 99 and the wafer 23 is positioned by the prober stage. Here, the prober control takes full responsibility for positioning a particular chip under the camera to produce a chip image as shown in FIG. 8B. The inspection process takes place on the virtual chip in memory. Thus, the indexing time from chip to chip is utilized for inspection making this a very efficient operation The post-probe embodiment can be adapted to printed circuit board (PCB) inspection by substituting a suitable handling and holding device for rectangular PCB's or films. The coarse inspection performed on the image data scanned into memory with direct positional relationship extract suspicious defect candidates. These are often resolvable at the scanner resolution level into harmless or damaging defects. In ambiguous cases the camera is moved in automatically to obtain the necessary details for a decision.

The post-probe inspection is usually planned as inspecting every wafer but at least initially only a limited number of chips. If the initially tested chips fail it may be desirable to conduct a 100% inspection. Only electrically good chips are inspected, thus, the main criteria is to locate defects which may cause failure during assembly or, more seriously, failure after the chip package is installed in the field.

The rules are set according to manual observation and judgments based on experience. The result from the gross defect inspection can also logically influence the sample selection for detailed inspection. FIG. 7B shows a critically positioned probe mark 97, which may have damaged the "glassification". The main performance advantage of the single die inspection is the clear and unambiguous classification in automatic mode using the MAMMEX criteria.

In the post-probe inspection station the wafer 23 is largely stationary after it is placed on the chuck 73 apart from minor corrective chuck motions to reach optimum focus during image scan-in. The scanner rail 75 on the other hand can move horizontally in the Y-direction 77 and the attached CCD camera 79 can be positioned in the X-direction 81. In terms of positional accuracy it must only be sufficient to locate any unique chip from the wafer map. The combined effect is the ability to scan in an image of the whole wafer and position the camera over any one uniquely identified chip. The single chip inspection station can equally well process previously inked wafers, using the wafer image as a direct map for picking "good" and "bad" chips for the inspection process.

After post-probe inspection the wafer can be optionally inked or have the map updated, then replaced in its original wafer storage cassette.

Other embodiments of the invention include running the loader inspection unit 13 as a separate, free-standing optical inspection system. The handler 21 will in this case only move wafers between the inspection units and storage. Such a system can be made to qualify for class 1 clean room operation. It is also possible to mount the post-probe inspection unit 19 in place of the probe card ring assembly 29, 31. In this case the prober becomes a dedicated optical inspection station which can alternate its operation with regular probing.

As shown in FIGS. 4A and 4B the image data reveals, when displayed, sufficient details to read the wafer ID 83, chip coordinate references 101, 103 and 105, special chips 107 and 109, process defects 89 and 91. While all information including chip size can be found by global search, the process is simplified by introducing standard data available from each wafer type. Normally this includes: Wafer sizes, chip size, flat orientation, wafer ID location and type. To simplify the inspection process it is also common to include the image of a typical standard chip 93. This sort of "training" is typically performed only once when the first wafer of this type appears. The data is then stored as part of the retrievable "set-up data" identified by the wafer type name.

Using a standard chip, such as the chip 93 shown in FIG. 4, as a model, the wafer image in memory is analyzed identifying each chip and classifying them. Depending on an established criteria a coordinate reference chip 101 is established and the adjacent chips recorded. In FIGS. 4A and 4B, chip 103 is marginal and 105 is partial. In this example, the chips are given a binary number based on the completeness of the image. The exact chip image is then stored in a separate memory location for future reference.

All special chips like 107 and 109 are recorded with image and pattern defects like 89 and 91 noted as defects as well as defining the chip as testable and not testable. Each defect is analyzed and reduced to a numerical value by a criteria based on human inspection methods. The resulting coordinate chip log, duly identified by the wafer ID 83 is the most efficient wafer map based on actual images. It maximizes the testable chips that are potentially good and minimizes total testing time. Since the wafer map created is based on actual images it is usable even after the chips are diced apart, thus, applicable to pick-and-place assembly operations.

The analysis technique is similar when the single chip image is reviewed. Each defect is extracted from the regular pattern and subjected to numerical analysis which is based on industry specification (customer modifiable) and skilled human inspection methodology. The MAMMEX procedures are adopted to give the desired extraction and classification reliability.

We claim:

1. In a method for investigating electronic circuit devices for manufacturing defects, the steps of:
   (a) converting intuitive criteria used to investigate an electronic circuit device for manufacturing defects to specific numerical criteria;
   (b) programming a computer with said criteria;
   (c) acquiring information in said programmed computer defining an electronic circuit device by scanning in an image of said device and operating on said virtual images rather than manipulating the physical device;
   (d) using said computer to apply said specific numerical criteria defined by said program to said information to identify regions of said electronic circuit device to be investigated, said information defining a manufacturing defect.

2. The method of claim 1 wherein said specific numeric criteria that are applied to segregated regions of said electronic circuit device having manufacturing defects which contain defect characteristics exceeding the standards required for further use of said regions of said electronic circuit device for processing into electronic circuit device products.

3. The method of claim 1 together with the step of introducing an image controlled coordinate reference system allowing individual electronic circuit devices to be reliably re-identified throughout the processing steps.

4. The method of claim 1 wherein said electronic circuit devices are semiconductor wafers together with the step of automatically generating a wafer map from a scanned wafer image requiring no physical manipulation of the wafer and using said map to position a CCD camera adjacent said wafer to obtain high resolution images for a detailed chip inspection.

5. The method of claim 1 wherein said electronic circuit devices are semiconductor wafers together with the step of aligning the wafer according to die pattern.

6. In a method for investigating semi-conductor wafers for manufacturing defects, the steps of:
   (a) acquiring information from an image defining said semi-conductor wafer with opto-electronic means, including the step of generating a digital representation of said image;
   (b) analyzing said information by applying pre-selected criteria to said information to identify regions of said semi-conductor wafer by said information having a manufacturing defect;
       said step of analyzing including detecting digital information in said representation defining manufacturing defects in said semi-conductor wafer, and
       detecting digital information in said representation defining said defects.

7. A gross defect, optical inspection unit for chips on a semiconductor wafers comprising:
   means for aligning the wafer according to the die pattern;
   means for generating a unique map for each wafer;
   means for sorting the chips by direct image analysis into testable and not testable categories; and
   means for selecting for further testing only those chips sorted as testable.

* * * * *